United States Patent
Foster

(10) Patent No.: US 6,217,559 B1
(45) Date of Patent: Apr. 17, 2001

(54) AUTOMATIC SAFETY SYRINGE CONSTRUCTION

(76) Inventor: Livingston Foster, 705 SW. 76th Ave., North Lauderdale, FL (US) 33068

( * ) Notice: Subject to any disclaimer, the term of this patent is extended or adjusted under 35 U.S.C. 154(b) by 0 days.

(21) Appl. No.: 09/595,919

(22) Filed: Jun. 13, 2000

(51) Int. Cl.$^7$ ..................................................... A61M 5/00
(52) U.S. Cl. ........................... 604/195; 604/198; 604/263
(58) Field of Search ................................... 604/187, 195, 604/263, 110, 198

(56) References Cited

U.S. PATENT DOCUMENTS

| | | |
|---|---|---|
| 5,512,050 | 4/1996 | Caizza et al. ........................ 604/263 |
| 5,527,294 | 6/1996 | Weatherford et al. ............... 604/198 |
| 5,554,130 | 9/1996 | McDonald et al. .................. 604/198 |
| 5,554,131 | 9/1996 | Lacivita ............................... 604/198 |

Primary Examiner—John D. Yasko
(74) Attorney, Agent, or Firm—Henderson & Sturm LLP

(57) ABSTRACT

A safety syringe construction (10) including a conventional syringe member (20) equipped with a fixed tubular male sleeve member (20) and spring biased moveable tubular female sleeve member (30) which is slidable relative to the tubular male sleeve member (30). The male (30) and female (40) sleeve members are provided with a locking unit (15) for releasably engaging the female sleeve member (40) relative to the male sleeve member (30).

4 Claims, 1 Drawing Sheet

AUTOMATIC SAFETY SYRINGE CONSTRUCTION

BACKGROUND OF THE INVENTION

1. Field of the Invention

The present invention relates to the field of automatic safety syringe constructions.

2. Description of Related Art

As can be seen by reference to the following U.S. Pat. Nos. 5,512,050; 5,527,294; 5,554,130; and 5,554,131, the prior art is replete with myriad and diverse safety syringe constructions.

While all of the aforementioned prior art constructions are more than adequate for the basic purpose and function for which they have been specifically designed, they do not represent the final word with regard to the design of devices of this type.

As all health care professionals are all too well aware, the greatest risk of infection to the health care giver involves the administration of an injection to the patient. The patient's bodily fluids can be transferred to the health care giver by careless handling of the sharp point of a hypodermic needle.

As a consequence of the foregoing situation, there has existed a longstanding need for a new and improved type of safety syringe construction involving a movable sleeve which is normally extended to cover the point of the needle when not in use, and which can be retracted to give the patient an injection, and the provision of such a construction is a stated objective of the present invention.

BRIEF SUMMARY OF THE INVENTION

Briefly stated, the safety syringe construction that forms the basis of the present invention comprises in general, a conventional syringe unit having a male sleeve unit, a female sleeve unit, a spring unit, and a locking unit.

As will be explained in greater detail further on in the specification, the male sleeve unit is fixedly secured to one portion of the syringe unit, the female sleeve unit is slidably disposed on the male sleeve unit, the spring unit is operatively connected on one end to the female sleeve unit, and operatively connected on the other end to another portion of the syringe unit such that the female sleeve unit in its extended position covers the pointed end of the syringe unit needle. The female sleeve unit can be retracted relative to the male sleeve unit to expose the needle for the purpose of giving a patient an injection.

In addition, the male and female sleeve units are further provided with a locking unit which can captively, yet releasably engage the female sleeve unit relative to the male sleeve unit in the retracted position.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
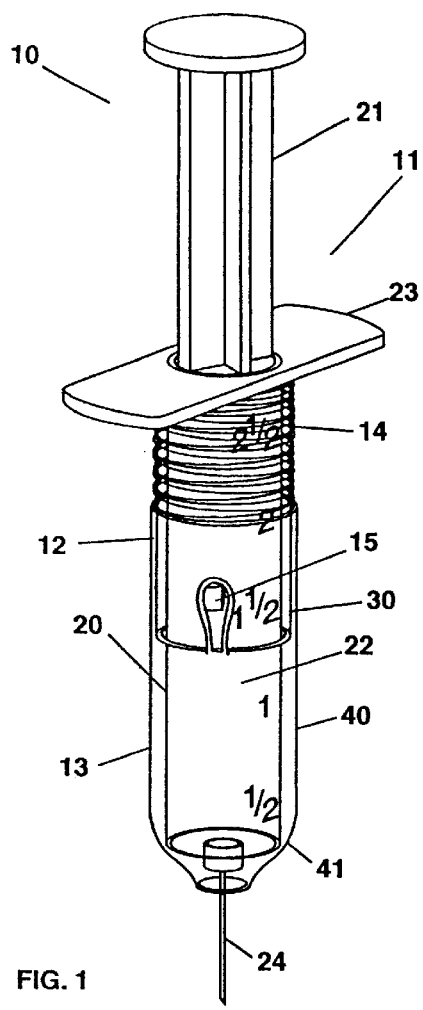
FIG. 1 is a perspective view of the protective sleeve units in the retracted position.

As can be seen by reference to the drawings, and in particular to FIG. 1, the automatic safety syringe construction that forms the basis of the present invention is designated generally by the reference number 10. The construction 10 includes a conventional syringe unit 11 provided with male 12 and female 13 sleeve units which are provided with a spring biasing unit 14 and a locking unit 15.

Figure 2:
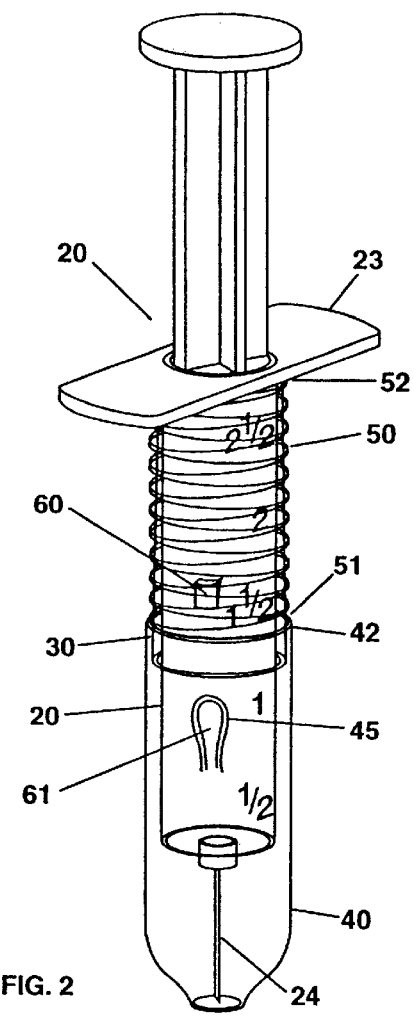
FIG. 2 is a perspective view of the protective sleeve units in the extended position.

As can best be seen by reference to FIGS. 1 and 2, the conventional syringe unit 11 comprises a syringe member 20 having a plunger element 21 slidably disposed in a medicinal reservoir 22 having a transverse flange 23 on the upper end and equipped with a hypodermic needle 24 on the lower end.

Still referring to FIGS. 1 and 2, it can be seen that the male 12 and female 13 sleeve units comprise respectively, a generally cylindrical tubular male sleeve member 30 fixedly secured to the exterior surface of the medicinal reservoir 22 and a generally cylindrical tubular female sleeve member 40 having a tapered lower end 41. The tubular female sleeve member 40 is slidably disposed on the tubular male sleeve member 30.

Figure 3:
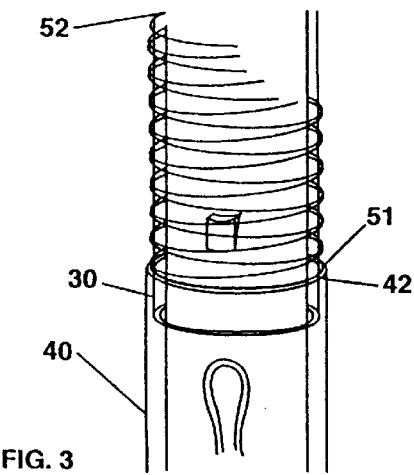
FIG. 3 is an isolated detail view of the protective sleeve units and the spring biasing unit.

In addition, as shown in FIGS. 1 through 3, the spring biasing unit 14 comprises a helical spring member 50 dimensioned to surround the male sleeve member 30 and having a lower end 51 which is fixedly secured to the upper end 42 of the female sleeve member 40 and has an upper end 52 which is fixedly secured to the underside of the transverse flange 23 of the syringe member 20.

Figure 4:
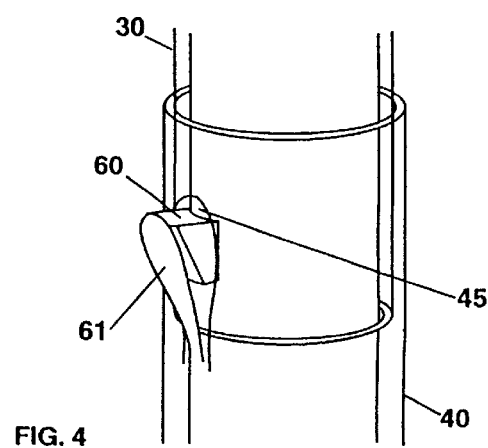
FIG. 4 is a cross sectional detail view showing the cooperation between the male and female locking elements of the locking unit.

As can best be seen by reference to FIGS. 2 and 4, the locking unit 15 comprises a tapered and outwardly projecting tab member 60 formed on the exterior surface of the male sleeve member 30 and a contoured hinged flap element 61 defining an opening 45 in the side of the female sleeve member 40.

As a consequence of the arrangement when the female sleeve member 40 slides upwardly relative to the male sleeve member 30, the tab 60 will force the flap element 61 outwardly such that the downward spring biasing action of the spring 50 will be arrested by the engagement of the tab 60 in the opening 45 in the female sleeve member.

Then after the patient has been given an injection, all the medical personnel have to do to automatically extend the retracted female sleeve member 40 is to press against the flap element 61 which displaces the tab 60 laterally so that the spring member 50 will return the female sleeve member 40 to its fully extended position relative to the male sleeve member 30 to cover the end of the needle 24.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A syringe construction comprising:

a conventional syringe member including a medicinal reservoir having an upper end provided with a transverse flange and a lower end provided with a hypodermic needle;

a tubular male sleeve member fixedly secured to said medicinal reservoir, and provided with an outwardly projecting tab;

a tubular female sleeve member dimensioned to slidably receive said tubular male sleeve member, and having an opening formed in the side of the tubular female sleeve member dimensioned to receive said tab; wherein, the female tubular sleeve member is laterally displaceable relative to the tubular male sleeve member to engage and disengage the tab relative to said opening; and a spring element disposed in a surrounding relationship relative to said tubular male sleeve member and having a lower end connected to the tubular female sleeve member and an upper end connected to the transverse flange on the conventional syringe member.

2. The construction as in claim 1 wherein said tab is tapered.

3. The construction as in claim 2 wherein said female sleeve member is provided with a hinged flap element disposed in said opening.

4. The construction as in claim 1 wherein the tubular female sleeve member has a lower end which is tapered.

* * * * *